(12) United States Patent
Greenberg et al.

(10) Patent No.: US 9,381,078 B2
(45) Date of Patent: Jul. 5, 2016

(54) POWER AND/OR SIGNAL TRIGGER WIRE FOR AN ENDOVASCULAR DELIVERY SYSTEM

(75) Inventors: Roy K. Greenberg, Bratenahl, OH (US); Karl J. West, Geneva, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 218 days.

(21) Appl. No.: 13/454,901

(22) Filed: Apr. 24, 2012

(65) Prior Publication Data

US 2012/0323300 A1 Dec. 20, 2012

Related U.S. Application Data

(60) Provisional application No. 61/480,931, filed on Apr. 29, 2011.

(51) Int. Cl.
| | |
|---|---|
| *A61F 2/84* | (2006.01) |
| *A61F 2/07* | (2013.01) |
| *A61B 19/00* | (2006.01) |
| *A61F 2/95* | (2013.01) |
| *A61F 2/89* | (2013.01) |

(52) U.S. Cl.
CPC .............. *A61F 2/07* (2013.01); *A61B 19/5244* (2013.01); *A61F 2/95* (2013.01); *A61B 2019/5251* (2013.01); *A61B 2019/5272* (2013.01); *A61B 2019/5458* (2013.01); *A61B 2019/5475* (2013.01); *A61F 2/89* (2013.01); *A61F 2002/9511* (2013.01)

(58) Field of Classification Search
CPC ................... A61B 19/5244; A61B 2019/5251; A61B 2019/5272; A61B 2019/5458; A61B 2019/5475; A61F 2002/9511; A61F 2/89; A61F 2/07; A61F 2/95
USPC ............... 623/1.11, 1.12, 1.13, 1.15; 606/200
See application file for complete search history.

(56) References Cited

U.S. PATENT DOCUMENTS

| 6,224,627 | B1 * | 5/2001 | Armstrong et al. | ........... 623/1.23 |
| 6,579,311 | B1 | 6/2003 | Makower | ...................... 623/1.23 |
| 6,592,526 | B1 * | 7/2003 | Lenker | .......................... 600/463 |

(Continued)

FOREIGN PATENT DOCUMENTS

| EP | 1 943 974 A1 | 7/2008 |
| EP | 2 085 108 A2 | 8/2009 |

(Continued)

OTHER PUBLICATIONS

Patent Examination Report No. 1, issued in Australian Patent Application No. 2012202482, dated Feb. 27, 2013, 3 pages.

(Continued)

*Primary Examiner* — Julie A Szpira
(74) *Attorney, Agent, or Firm* — Brinks Gilson & Lione

(57) ABSTRACT

An endovascular graft delivery system includes an endovascular prosthetic device and one or more trigger wires deployably engaging portions of the endovascular prosthetic device. An electrical element is positioned at a proximal end of a trigger wire. The electrical element is in signal communication with the trigger wire to communicate operational signals over the trigger wire. The operational signals may be power or control signals to assist with positioning the endovascular prosthetic device at a desired deployment location.

17 Claims, 4 Drawing Sheets

(56) References Cited

U.S. PATENT DOCUMENTS

| | | | |
|---|---|---|---|
| 7,232,459 B2 | 6/2007 | Greenberg et al. | 623/1.13 |
| 7,407,509 B2 | 8/2008 | Greenberg et al. | 623/1.35 |
| 7,611,529 B2 | 11/2009 | Greenberg et al. | 623/1.11 |
| 8,221,494 B2* | 7/2012 | Schreck et al. | 623/1.35 |
| 2004/0054403 A1 | 3/2004 | Israel | |
| 2004/0073286 A1* | 4/2004 | Armstrong et al. | 623/1.12 |
| 2006/0004433 A1 | 1/2006 | Greenberg et al. | 623/1.11 |
| 2006/0276883 A1 | 12/2006 | Greenberg et al. | 623/1.31 |
| 2007/0100415 A1 | 5/2007 | Licata et al. | 623/1.11 |
| 2007/0123910 A1 | 5/2007 | Hartley et al. | 606/108 |
| 2007/0270650 A1 | 11/2007 | Eno et al. | 600/145 |
| 2007/0276461 A1 | 11/2007 | Andreas et al. | 623/1.11 |
| 2008/0139915 A1 | 6/2008 | Dolan et al. | 600/407 |
| 2008/0177139 A1 | 7/2008 | Courtney et al. | |
| 2008/0188921 A1* | 8/2008 | Yamasaki et al. | 623/1.13 |
| 2009/0048663 A1 | 2/2009 | Greenberg | 623/1.35 |
| 2009/0179632 A1 | 7/2009 | Nishiguchi et al. | 324/207.25 |
| 2009/0222078 A1 | 9/2009 | Greenberg | 623/1.13 |
| 2010/0268204 A1 | 10/2010 | Tieu et al. | 606/27 |
| 2010/0280363 A1 | 11/2010 | Skarda et al. | 600/424 |

FOREIGN PATENT DOCUMENTS

| | | | |
|---|---|---|---|
| WO | WO 2007/058872 A2 | 5/2007 | |
| WO | WO 2008/091409 A1 | 7/2008 | |
| WO | WO 2010/056302 A2 | 5/2010 | |

OTHER PUBLICATIONS

Patent Examination Report No. 1, issued in Australian Patent Application No. 2012202484, dated Mar. 13, 2013, 4 pages.

European Search Report in European Patent Application No. 12275050.8, document No. EP 2 517 677, published Oct. 31, 2012, 20 pages.

European Search Report in European Patent Application No. 12275051.6, document No. EP 2 517 665 A1, published Oct. 31, 2012, 20 pages.

Copy of an Office Action issued in U.S. Appl. No. 13/454,821, dated May 16, 2014, 12 pages.

* cited by examiner

POWER AND/OR SIGNAL TRIGGER WIRE FOR AN ENDOVASCULAR DELIVERY SYSTEM

CROSS REFERENCE TO RELATED APPLICATIONS

This application claims priority under 35 U.S.C. §119(e) to U.S. provisional application No. 61/480,931, filed on Apr. 29, 2011, pending, which application is incorporated herein in its entirety by this reference.

TECHNICAL FIELD

The present invention relates generally to a medical device. More particularly, the present invention relates to a power and/or signal trigger wire for an endovascular delivery system.

BACKGROUND

Throughout this specification, when discussing the application of this invention to the aorta or other blood vessels, the term "distal", with respect to a prosthesis, is intended to refer to a location that is, or a portion of the prosthesis that when implanted is, further downstream with respect to blood flow; the term "distally" means in the direction of blood flow or further downstream. The term "proximal" is intended to refer to a location that is, or a portion of the prosthesis that when implanted is, further upstream with respect to blood flow; the term "proximally" means in the direction opposite to the direction of blood flow or further upstream.

The functional vessels of human and animal bodies, such as blood vessels and ducts, occasionally weaken or even rupture. For example, the aortic wall can weaken, resulting in an aneurysm. Upon further exposure to hemodynamic forces, such an aneurysm can rupture. In Western European and Australian men who are between 60 and 75 years of age, aortic aneurysms greater than 29 mm in diameter are found in 6.9% of the population, and those greater than 40 mm are present in 1.8% of the population.

One surgical intervention for weakened, aneurismal, or ruptured vessels involves the use of a prosthetic device to provide some or all of the functionality of the original, healthy vessel, and/or preserve any remaining vascular integrity by replacing a length of the existing vessel wall that spans the site of vessel failure. One such prosthetic device is a stent graft. Stent grafts are used for treatment of vasculature in the human or animal body to bypass a repair or defect in the vasculature.

A length of a vessel which is treatable by such prosthesis may have one or more branch vessels, i.e. vessels anastomosed to the main vessel. The celiac artery, superior mesenteric artery, left common carotid artery, and renal arteries, for example, are branch vessels of the aorta; the hypogastric artery is a branch vessel of the common iliac artery. Thus, a stent graft may be used to span an aneurism which has occurred in or is associated with the primary artery. Bypassing such a branch vessel without providing blood flow into it can cause problems and hence it has been proposed to provide a fenestration or side branch on a stent graft which when deployed is positioned over the opening to the primary artery and then another stent graft can be deployed through the fenestration or side branch into the secondary artery to provide a blood flow path to the secondary artery.

When treating a vessel with a prosthetic device, it is therefore preferable to preserve the original circulation by providing a prosthetic branch that extends from the prosthesis to a branch vessel so that the blood flow into the branch vessel is not impeded. For example, the aortic section of one abdominal aortic prosthesis can be designed to extend above the renal arteries and to have prosthetic branches that extend into the renal arteries. Branch extension prosthetic modules ("branch extensions") can form a tromboning connection to the prosthetic branch to complete the prosthesis. Furthermore, some aneurysms extend into the branch vessels themselves. Deploying prosthetic branches and branch extensions into these vessels may help prevent expansion and/or rupture of these extended aneurysms.

Another example of a vessel that may be treated with a stent graft is the aortic arch. Aortic arch stent grafts are used in treating dissection and aneurismal dilation of the aortic arch. As with other primary vessels, many of these grafts have branches that maintain the patency of the branch arteries originating in the aortic arch. These branch arteries include the innominate artery, the left common carotid artery, and the left subclavian artery. A stent graft in the aortic arch may itself be branched to help direct the flow of blood into these branch arteries. Many of these branched grafts have branches that project outward from the prosthesis. Implanting the stent grafts in the branch arteries provides a challenge to surgeons because of the anatomic features of the aortic arch. Blood flow from the branch arteries must not be interrupted for an extended length of time because the branch arteries supply blood to the brain. Implanting branch stents that mate with the branches presents challenges because the natural orientation of the aortic arch must be matched or simulated by the stent grafts.

A surgeon may access the aortic arch through the branch arteries to implant small vessel stents. Guide wires are used to link the small vessel stents in the branch arteries with the branches of the aortic arch stent. However, much time may be lost in threading the guide wires through the openings of the aortic arch stent branches and through the branch arteries. A surgeon will often manipulate the guide wire around the difficult angles in the aortic arch stent channels before being able to connect with the delivery catheter of the branched stent.

In general, manipulating guide wires to correctly and reliably position a medical device such as a stent graft requires the surgeon's utmost skill and experience. The surgeon has relatively little information available defining where the medical device is positioned, its orientation and alignment. Conventionally, fluoroscopy has been used by surgeons to obtain real-time moving images of a patient's anatomy. However, the use of x-rays for fluoroscopy poses a health risk to the patient, surgeon and other medical personnel. Because of small geometries, placement accuracy can be critical, particularly when positioning a device such as a stent graft in relation to another vessel such as a branch artery. There is therefore a need for an improved method and device for providing information to the surgeon about the position and orientation of the medical device. Moreover, there is a need for doing so using safer techniques that reduce the use of fluoroscopy.

BRIEF SUMMARY

In a first aspect, the present disclosure provides an endovascular graft delivery system including an endovascular prosthetic device and one or more trigger wires deployably engaging portions of the endovascular prosthetic device. An electrical element is positioned at a proximal end of a trigger wire. The electrical element is in signal communication with the trigger wire to communicate one or more operational signals with the trigger wire. The operational signal may be a power or a control signal to assist with positioning the endovascular prosthetic device at a desired deployment location. The operational signal may be an electrical signal such as current or voltage conveyed on one or more conducting wires or may be an optical signal conveyed on one or more optical fibers. The trigger wire may include one or more electrical conductors, one or more optical fibers and mechanical strain relief bundled together in a single trigger wire structure. The operational signal may be an analog signal or a digital signal or may be digital data conveyed on a single wire or a multiple-wire bus. In one example, the electrical element includes a sensor to provide information about the position of the endovascular prosthetic device during deployment of the endovascular prosthetic device. The information is detectable over the trigger wire at a location outside the body of the patient. The electrical element may be a transmitter responsive to an operational signal received over the trigger wire to emit a positioning transmission. The emitted transmission may be radio frequency energy, magnetic energy or light. In a particular application, the endovascular prosthetic device is an aortic stent graft.

In a second aspect, the present disclosure provides a method for deploying an endovascular prosthetic device. The method includes transvascularly positioning the endovascular prosthetic device near a desired deployment location in a body of a patient and applying a signal to a trigger wire in mechanical engagement with the endovascular prosthetic device. The trigger wire is in signal communication with an electrical element associated with the endovascular prosthetic device. Also, the trigger wire releasably constrains a mechanical aspect of the endovascular prosthetic device during the positioning of the endovascular prosthetic device. The method further includes, at a detector outside the body, detecting an electromagnetic positioning transmission transmitted by the electrical element based on the applied signal. In response to the detected electromagnetic positioning transmission, the endovascular device may be re-positioned. Then, another signal may be applied to the trigger wire; and a subsequent electromagnetic positioning transmission detected at the detector. When the endovascular prosthetic device is at the desired deployment location, the trigger wire may be activated to release a mechanical constraint of the endovascular prosthetic device and thereby deploy the endovascular prosthetic device at the desired deployment location.

In a third aspect, the present disclosure provides a method for an endovascular prosthetic device. The method includes transvascularly positioning an endovascular prosthetic device near a desired deployment location in a human body and positioning two or more electrical elements adjacent to the endovascular prosthetic device. The two or more electrical elements are in signal communication with two or more respective trigger wires and are electrically responsive to an activation signal conveyed by the respective trigger wires to transmit respective electromagnetic positioning transmissions which are detectible outside the human body. The method further includes providing the activation signal to the two or more trigger wires to activate the two or more electrical elements and detecting initial positioning transmissions to identify an initial position for the endovascular prosthetic device. The method further includes subsequently positioning the endovascular prosthetic device and providing a subsequent activation signal to activate the two or more electrical elements and detecting subsequent positioning transmissions responsive to the subsequent electromagnetic identifications to identify a movement of the endovascular prosthetic device.

In a further aspect, the present embodiments provide an endovascular graft delivery system including an endovascular graft positionable in a human body. The delivery system further includes one or more electrical elements responsive to an applied operational signal to transmit an electromagnetic transmission. The one or more electrical elements are positioned at a proximal end of the endovascular graft delivery system. The delivery system further includes one or more trigger wires, each respective trigger wire in signal communication with a respective electrical element to provide the operational signal to the respective electrical elements. Each respective trigger wire engages a portion of the endovascular graft to remove a mechanical constraint from the endovascular graft upon triggering. In a particular embodiment, the one or more trigger wires exit a distal end of the endovascular graft delivery system. The delivery system may further include a receiver external to the human body operative to receive the transmitted electromagnetic transmission and a display device coupled with the receiver to produce a positioning image based on the received electromagnetic transmission and stored data about the human body. The trigger wires may include electrical conductors or optical fibers or both to convey the operational signal to the electrical element. The electrical conductors and optical fibers may be bundled with the trigger wire.

DETAILED DESCRIPTION OF THE PRESENTLY PREFERRED EMBODIMENTS

Figure 1:
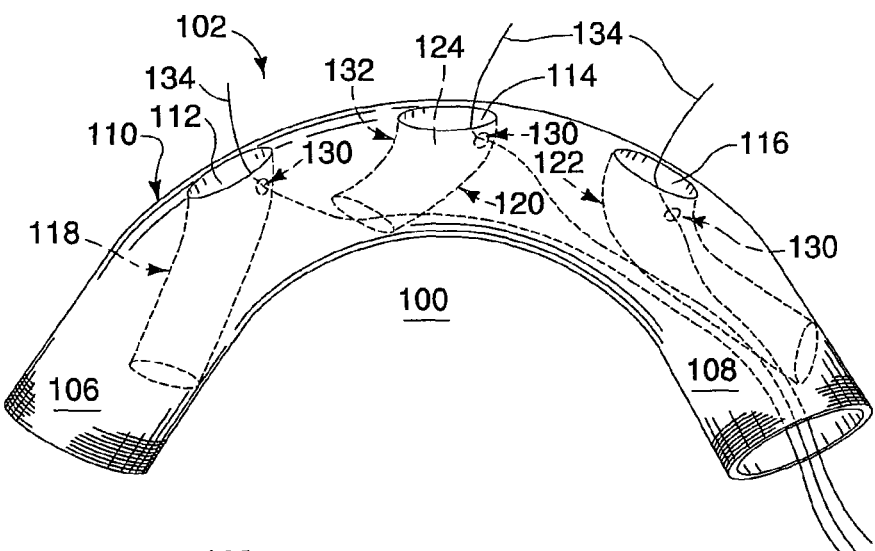
FIG. 1 shows a first embodiment of an endovascular prosthetic device

The term "endoluminal" describes objects that are found or can be placed inside a lumen in the human or animal body. The term "endovascular" describes objects that are within a blood vessel. A lumen can be an existing lumen or a lumen created by surgical intervention. This includes lumens such as blood vessels, parts of the gastrointestinal tract, ducts such as bile ducts, parts of the respiratory system, etc. A "prosthetic device" is a prosthesis that can be placed inside one of these lumens.

The term "stent" means any device or structure that adds rigidity, expansion force, or support to a prosthesis. A Z-stent is a stent that has alternating struts and peaks (i.e., bends) and defines a generally cylindrical lumen. The "amplitude" of a Z-stent is the distance between two bends connected by a single strut. The "period" of a Z-stent is the total number of bends in the Z-stent divided by two, or the total number of struts divided by two.

The term "endoleak" refers to a leak around or through a prosthetic device. Endoleaks can occur through the fabric of a prosthesis, through the interconnections of a modular prosthesis, or around the ends of the prosthesis, inter alia. Endoleakage may result in the repressurizing of an aneurysm.

The term "branch vessel" refers to a vessel that branches off from a main vessel. Examples are the celiac and renal arteries which are branch vessels to the aorta (i.e., the main or primary vessel in this context). As another example, the hypogastric artery is a branch vessel to the common iliac, which is a main or primary vessel in this context. Thus, it should be seen that "branch vessel" and "main vessel" or "primary vessel" and "secondary vessel" are relative terms.

Some embodiments of the endovascular prosthetic system of the present invention include a prosthetic device having structural support. In some embodiments this structural support is a stent. In one embodiment, the stent may be formed by a plurality of discontinuous stent elements. In another embodiment, the stent may be formed from a single stent element. The stent may be located on the exterior of the device, the interior of the device, or both. The stent may be balloon-expandable or a self-expanding stent. Typically, the stent has a circular cross-section when fully expanded so as to conform to the generally circular cross-section of a body lumen. In one example, the stent may comprise struts and acute bends or apices that are arranged in a zigzag configuration in which the struts are set at angles to each other and are connected by the acute bends. The present invention can be used with a wide variety of stent configurations, including, but not limited to, shape memory alloy stents, expandable stents, and stents formed in situ. Preferably, the stent is formed from nitinol, stainless steel or another biocompatible metal or alloy, though any suitable material may be used.

The term "stent graft" refers to a type of endoluminal device made of a tubular graft material and supported by at least one stent. The stent graft material is preferably made of woven polyester having a twill weave and a porosity of about 350 ml/min/cm$^2$ (available, for example, from Vascutek Ltd., Renfrewshire, Scotland, UK). Any other suitable material may be used.

As noted, stent grafts may be either self-expanding or balloon-expandable, or they can have characteristics of both types of stent grafts. Self-expanding stent grafts may be delivered to a target site in a compressed configuration and subsequently expanded by removing a delivery sheath, removing trigger wires and/or releasing diameter reducing ties. With self-expanding stents, the stents expand primarily based on their own expansive force without the need for further mechanical expansion. In a stent made of a shape-memory alloy such as nitinol, the shape-memory alloy may be employed to cause the stent to return to a predetermined configuration upon removal of the sheath or other device maintaining the stent in its predeployment configuration.

When trigger wires are used as a deployment control mechanism, the trigger wires may releasably couple the proximal and/or distal ends of a stent or stent-graft to a delivery catheter. Typically, one or more trigger wires are looped through a portion of the stent near a vertex of the stent. For example, trigger wires may be used to restrain a "Z-stent" or Gianturco stent comprising a series of substantially straight segments interconnected by a series of bent segments. The trigger wires may be disposed through, and pull upon, the bent segments to pull the stent closely against the delivery catheter.

Trigger wires also may be used in conjunction with different stent designs, such as cannula-cut stents having relatively acute or pointed bends. The designs of cannula-cut stents may facilitate compression of the stent to a relatively small delivery profile due to the tight bends of the apices. With such stents, the trigger wires may be looped around one or more vertices formed beneath the proximal and/or distal apices, e.g., a location where an individual apex splits into two separate strut segments.

Referring now to the drawings, FIG. 1 shows a prosthetic device 100. The prosthetic device 100 is presented as exemplary only so as to illustrate generally the relevant structures and functions of a device with which the presently disclosed features may be used. These structures and functions may be used in conjunction with the widest variety of devices and the illustrated examples should not limit the extension of these structures and functions to other implementations.

The prosthetic device 100 has a primary prosthesis 102 including a major lumen 104 extending therethrough from the proximal end 106 to the distal end 108 of the primary prosthesis 102. The prosthetic device 100 has a major wall 110. The major wall 110 defines the major lumen 104 and occludes an aneurysm once deployed. First opening 112, second opening 114, and third opening 116 are shown in the major wall 110 that correspond to the first socket 118, second socket 120, and third socket 122 and to three branch arteries that branch away from the vessel in which the primary prosthesis 102 is deployed. Although the illustrated embodiment has three sockets, other embodiments of the present invention provide primary prostheses with one or two openings corresponding to one or two sockets. In other embodiments, there is at least one socket in the major wall 110. In yet other embodiments, the prosthetic device 100 has no sockets but features one or more fenestrations for purposes such as joining the prosthetic device to another prosthetic device to form a modular prosthesis. There are also embodiments wherein the primary prosthesis 102 further comprises a structural support around at least a portion of the major wall 110. The structural support may be a stent in some embodiments.

At least a portion of the first socket 118, second socket 120, and third socket 122 extend into the major lumen 110 from the openings 112, 114, and 116. While the first socket 118 and second socket 120 are angled in a proximal direction, the third socket 122 is angled in a distal direction in the figure shown. The sockets, therefore, are arranged in fluid communication with the major lumen 110. There may be other embodiments in which the sockets are angled in directions suitable for other specified treatments. The first socket 118, second socket 120, and third socket 122 mate with the proximal ends of secondary prostheses to form a secure seal with the primary prosthesis 102 at the openings. The sockets 118, 120, 122 are angled to receive the flow of blood and direct it through their minor lumens 124 into the branch arteries. The sockets 118, 120, 122 have fenestrations 130 that are in fluid communication with the minor lumens 124 and the major lumen 110. The fenestrations 130 are located in the distal side 108 of the minor walls 132 of the sockets, the portion that extends into the major lumen 110.

Although FIG. 1 illustrates an embodiment with three sockets 118, 120, 122, there are other embodiments comprising at least one socket or two sockets. In the embodiment illustrated, there is a first socket 118 and opening 112 configured to direct blood flow into the innominate artery when the prosthetic device 100 is positioned in the aortic arch of a human patient. The second socket 120 and opening 114 are configured to direct blood flow into the left common carotid artery when the prosthetic device 100 is positioned in the aortic arch of a human patient. The third socket 122 and opening 116 are configured to direct blood flow into the left subclavian artery when the prosthetic device 100 is positioned in the aortic arch of a human patient.

Guide wires 134 extend from the distal end 108 of the primary prosthesis 102 through the fenestrations 130 to extend into the minor lumens 124 of the sockets and out of the primary prosthesis 102 through the openings in the major wall 110. Because of their arrangement in the present invention, upon placement and deployment, the guide wires 134 will be positioned in the target vessels for snaring with a double lumen catheter or some other guide wire. The guide wires 134 can have angled tips, flexible tips, compliant tips, or blunt tips.

Figure 2:
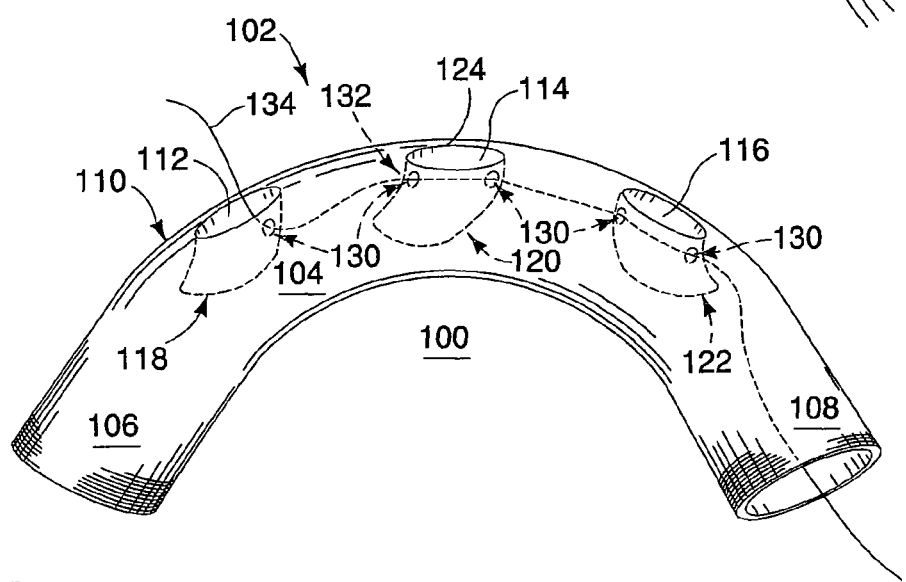
FIG. 2 shows a second embodiment of an endovascular prosthetic device.

FIG. 2 shows an embodiment having one guide wire 134 threaded through the fenestrations 130 of the first 118 socket, second socket 120 and third socket 122. Although the embodiment shown has two fenestrations 130 on the second socket 120 and third socket 122, there may also be embodiments having only one fenestration 130 per socket. The guide wire 134 is used to guide and deploy a secondary prosthesis, such as a side branch graft, into the first opening 112 of the first socket 118. After deployment of the first secondary prosthesis, the guide wire 134 is pulled out of the first socket 118 and into the second branch 120. In such an embodiment, the tip of the guide wire 134 preferably is formed of a shape memory alloy such as nitinol. This allows the tip of the guide wire 134 to assume an orientation pointing out of the second opening 124.

The fenestrations 130 in the branches do not hinder blood flow once the prosthesis 100 is properly deployed. Once a secondary prosthesis such as a tubular side branch graft prosthesis is positioned and deployed in a socket, the guide wire 134 is retracted from the fenestration 130. The proximal end of the secondary prosthesis occludes the fenestration 130 such that blood flow is not detrimentally affected.

The endovascular prosthetic device of FIGS. 1 and 2 can be deployed into the aortic arch of a human patient by methods known in the art. Generally, a primary prosthesis is introduced into an aortic arch having a aneurysm or other pathology. A main guide wire is inserted into the femoral artery (right or left) through an incision and is guided through the descending aorta, the aortic arch, and the ascending aorta. The main guide wire is guided to the aortic valve of the heart in some methods.

Subsequently, the primary prosthesis is partially expanded, for example by releasing constraints which form ties partially constraining the prosthesis. In the case of the device of FIG. 1 or of FIG. 2, first opening 112, second opening 114, and third opening 116 are aligned with the innominate artery, the left common carotid artery and the left subclavian artery, respectively. The guide wires are appropriately positioned in the arteries for snaring. Diagnostic imagining can be used to confirm the proper placement of all the elements. Conventionally, radiopaque markers can be placed to mark positions of the first opening 112, second opening 114 and third opening 116. Further, radiopaque markers can be placed at other locations on the primary prosthesis to assist in marking the position of the device. The prosthetic device is implanted and positioned using a suitable endovascular graft delivery system.

Figure 3:
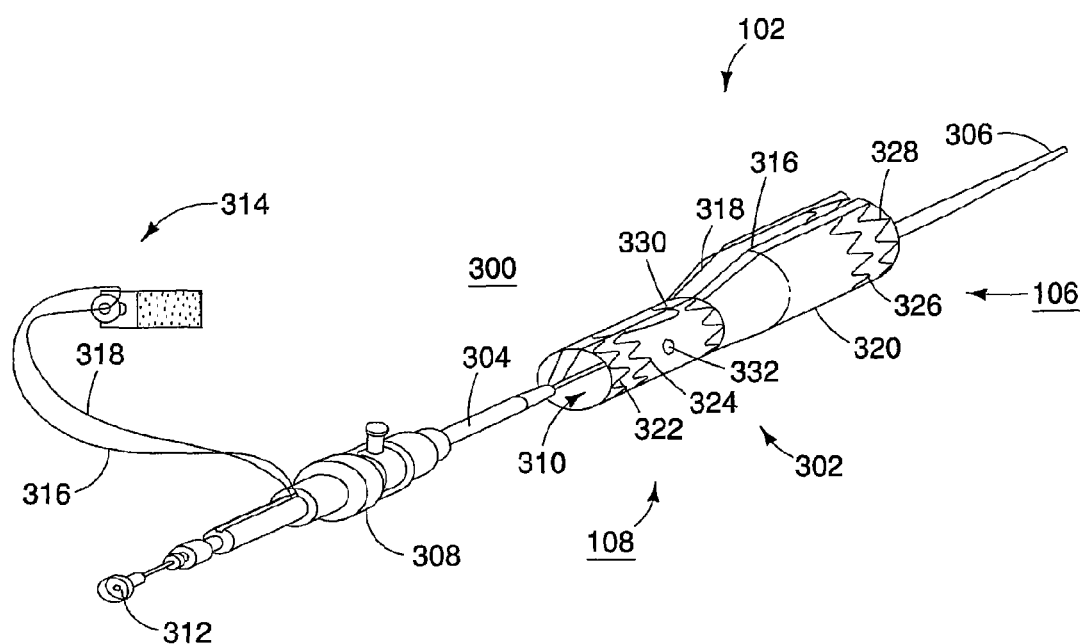
FIG. 3 shows and endovascular graft delivery system.

FIG. 3 shows an endovascular graft delivery system 300. The endovascular graft delivery system 300 includes an endovascular prosthetic device 302, a sheath 304, a proximal tapered nose cone dilator 306, a handle 308, a connector 312, an electrical device 314, a first trigger wire 316 and a second trigger wire 318. This embodiment is exemplary only. Alternative embodiments may include additional elements or may delete or modify some of the elements illustrated in FIG. 3. The endovascular graft delivery system 300 may be modified so as to be adapted to a particular purpose, function or anatomy. The endovascular graft delivery system 300 illustrated in FIG. 3 is particularly suited to deployment of an aortic stent graft to repair an aortic aneurysm in the ascending aorta, the descending aorta or the aortic arch of a human patient. Extensions to other applications will be apparent.

The endovascular prosthetic device 302 in the illustrated embodiment is an aortic stent graft. The endovascular prosthetic device 302 includes a tubular body 320 made of a biocompatible graft material and at least one stent. The endovascular prosthetic device 302 may be formed from a single material, a blend of materials, a weave, a laminate or a composite or two or more materials. The tubular body 320 defines a major lumen 310. The tubular body 320 may be shaped to accommodate particular anatomical configurations. For example, the tubular body 320 may define one or more openings similar to openings 112, 114, 116 in the prosthesis 102 of FIG. 1. Such openings may be adapted to form minor lumens with branch grafts that are surgically implanted along with the endovascular prosthetic device 302. As will be appreciated by those of ordinary skill, the particular material and configuration, including openings and shape, of the endovascular prosthetic device 302 may be adapted in any suitably manner to fulfill particular requirements.

In the exemplary embodiment, the endovascular prosthetic device 302 includes first stent 322, second stent 324, third sent 326 and fourth stent 328. The stents 322, 324, 326, 328 may be of any configuration. In the exemplary embodiment, Z-stents are used. A Z-stent is a stent that has alternating struts and peaks (i.e., bends) and defines a generally cylindrical lumen. The stents 322, 324, 326, 328 may be balloon expandable or self-expanding. The stents have a circular cross-section when fully expanded so as to conform to the generally circular cross-section of a body lumen such as the aorta of the human body.

The endovascular prosthetic device 302 further includes one or more electrical elements 330 and a fenestration 332. As will be described in greater detail below, the electrical elements 330 are in electromagnetic or optical communication with trigger wires 316, 318. The electrical elements 330 may receive power or signals over the trigger wires 316, 318 or signals from the electrical elements 330 may be provided to the trigger wires. The fenestration 332 may be located in any suitable location and be used for any suitable purpose during deployment and subsequent use of the endovascular prosthetic device 302. In alternative embodiments, the electrical elements 330 may be in electrical or optical contact with a guide wire such as the guide wire 134 of FIGS. 1 and 2.

The sheath 304 is generally coaxial with the endovascular prosthetic device 302. The sheath 304 is slideable between two positions. Prior to and during implantation of the endovascular prosthetic device 302, the sheath 304 is in an initial proximal position with the undeployed endovascular prosthetic device 302 contained within the sheath 304. During this time, the delivery system 300 including the endovascular prosthetic device 302 may be introduced into the vasculature of a patient such as through an incision to access an iliac artery of the patient. When the endovascular prosthetic device 302 is properly positioned, the sheath 304 may be retracted to the position shown in FIG. 3 and the endovascular prosthetic device 302 deployed.

The proximal tapered nose cone dilator 306 forms the leading edge of the delivery system 300. The proximal end of the dilator 306 is tapered for accessing and dilating a vascular access site over a guide wire, such as the guide wires 134 of FIGS. 1 and 2. Such a guide wire is inserted in a vessel with an introducer needle. The guide wire may be maneuvered into position at a desired vascular location. The dilator 306 may then be maneuvered into position over the guide wire.

The handle 308 provides control of delivery system 300 during deployment of the endovascular prosthetic device 302. The handle 308 includes dilator control for sliding the dilator between the distal and proximal positions during deployment. The handle 308 includes trigger wire release arrangements 334 for releasing the trigger wires 316, 318, as will be discussed in further detail below.

The connector 312 permits mechanical connection to other equipment such as syringes and other medical apparatus. In that regard, a standardized connector may be used so that a wide variety of apparatus can be quickly and reliably coupled with the delivery system 300. An exemplary connector is a Luer-lok® connector hub. Any other suitable connector system may be provided for mechanical or fluidic connection to other equipment. In addition to the connector 312 for mechanical connection and fluidic communication, the connector 312 may include an electrical connector or an optical connector.

The trigger wires 316, 318 selectively provide mechanical, electrical and optical control of the endovascular graft delivery system 300. The endovascular prosthetic device 302 includes mechanical constraints of the type known in the art. The mechanical constraints can be selectively released by activating one or more of the trigger wires. The mechanical constraints maintain the endovascular prosthetic device 302 in a fully or partially collapsed configuration prior to and during deployment of the endovascular prosthetic device 302. In the collapsed configuration, the endovascular prosthetic device 302 is sufficiently small to be introduced into the vascular system to the desired deployment location. When properly located, for example, at the site of an aortic aneurysm, the trigger wires may be selectively activated to thereby release the constraints. Under force of stents 322, 324, 326, 328 or other device such as a balloon, the endovascular prosthetic device 302 expands to fill the vascular space.

In FIG. 3, the proximal end of the stent graft is shown fully deployed and the distal end of the stent graft is shown partially deployed. In many applications, two or more trigger wires attach the stent graft proximally and one trigger wire attaches the stent graft distally, although only two proximal trigger wires are illustrated in the drawing figure. Also, while the drawing figure shows the trigger wires 316, 318 disposed on the outside of the endovascular prosthetic device 302, one or more of the trigger wires 316, 318 may be disposed on the inside, in the lumen 310. The number and location of trigger wires and their arrangement may be tailored to the particular application for which the endovascular prosthetic device 302 is intended.

The trigger wires 316, 318 exit the distal end of the delivery system 300, distal to the handle 308. Other arrangements for engaging the trigger wires 316, 318 by the delivery system may be substituted. For example, one or more connector portions may be added to the connector 312 or to another connector. The connector portions may provide quick engage and disengage connections that are reliable for the type of signals involved, such as electrical and optical signals, without introducing interference to the conductors of the signal wire or other elements in the environment. The trigger wires are coupled with the electronic device 314. For ease and reliability of connection, a standard electrical or optical connector may be used to join the trigger wires 316, 318 and the electronic device 314. Additional mechanical strain relief may be provided as well.

The electronic device 314 is electromagnetically or optically coupled to the trigger wires 316, 318. The electronic device 314 may be any type of electrical apparatus arranged to cooperate with the electrical elements 330 disposed on the endovascular prosthetic device 302. The electronic device 314 may, for example, be a power supply, a signal generator, a signal detector, a display, etc. The nature of the electronic device 314 is thus related to the nature of the electronic elements 330 disposed on the endovascular prosthetic device 302.

The electrical elements 330 can include sensors or transmitters or other devices or combinations. In a first example, sensors may detect one or more conditions and, based on the detected condition, provide signals electrically to the trigger wires 316, 318. Upon sensing or detecting a condition, the sensor may provide feedback information to the trigger wire when the endovascular prosthetic device is positioned in the body of a patient. For example, the electrical element may sense electromagnetic energy impinging on the sensor from outside the body of the patient or from another internal location and may in response provide feedback information to the trigger wire. The feedback information maybe an analog signal, a digital signal or digital data produced or detected by the electrical element. In another example, sensors may be powered by electrical signals applied to the trigger wires 316, 318. In another example, a power signal may be applied to the trigger wires and thereby provided to the electrical elements 330 to provide operational power to the electrical elements 330. In yet another example, the electrical elements 330 may include a passive device such as a magnet producing a magnetic field which may be sensed in the vicinity of the electrical elements 330.

In some examples, the electrical elements may sense conditions such as a pressure, temperature or the strength of a nearby magnetic or electrical field, and produce an indication of the sensed condition. The indication may be conveyed on the electrical wire or optical fiber, for example as feedback information. The feedback information may be useful to the surgeon for positioning the endovascular prosthetic device. Thus, the electrical elements 330 can be used in conjunction with the trigger wires 316, 318 and the electronic device 314 to produce a display for a surgeon to use in positioning the prosthetic device 102 in a patient.

For example, in one embodiment, the electrical elements are responsive to radio frequency energy emitted at particular frequencies, each element responsive to a particular frequency. To position the prosthesis in the aortic arch, transmitters may be positioned in the innominate artery, the left common carotid artery and the left subclavian artery. Each transmitter transmits radio frequency energy at a particular, known frequency. As the electrical elements are advanced by the delivery system 300 through the descending aorta through the aortic arch, each respective electrical element detects the signal strength of the radio frequency transmission from the nearby transmitter and produces an indication related to the detected signal strength. By suitably processing this information, a graphical display or other information may be provided to the surgeon implanting the prosthetic device 102. The displayed information may give an indication of the axial proximity as well as the rotational proximity of the prosthetic device 102 to a desired deployment location.

The electrical elements 330 may alternatively or in addition include optical elements, such as optical sensors, cameras, and a light source. In such an embodiment, the trigger wires 316, 318 include optical fibers for conveying optical signals and information between the electrical elements 330 and the electronic device 314. The optical fibers may be bundled with electrical conductors in the trigger wire. The trigger wire may further include a mechanical actuator which is mechanically coupled to the constraints of the endovascular prosthetic device 302. In such an embodiment, the mechanical actuator provides strain relief so that when the trigger wire 316, 318 is pulled to remove the constraint, the mechanical actuator bears the mechanical load rather than the electrical conductors or the optical fibers. The constituent elements of the trigger wire may thus be tailored to accommodate the electrical elements 330 being employed with the endovascular prosthetic device 302. In yet another embodiment, a guide wire which is used to introduce the stent graft to the patient's vascular system may be used as a reference point for positioning the stent graft. For example, all or part of the guide wire may be energized with an electrical or magnetic signal. Presence of the signal may be detected to verify the position and orientation of the stent graft.

Figure 4:
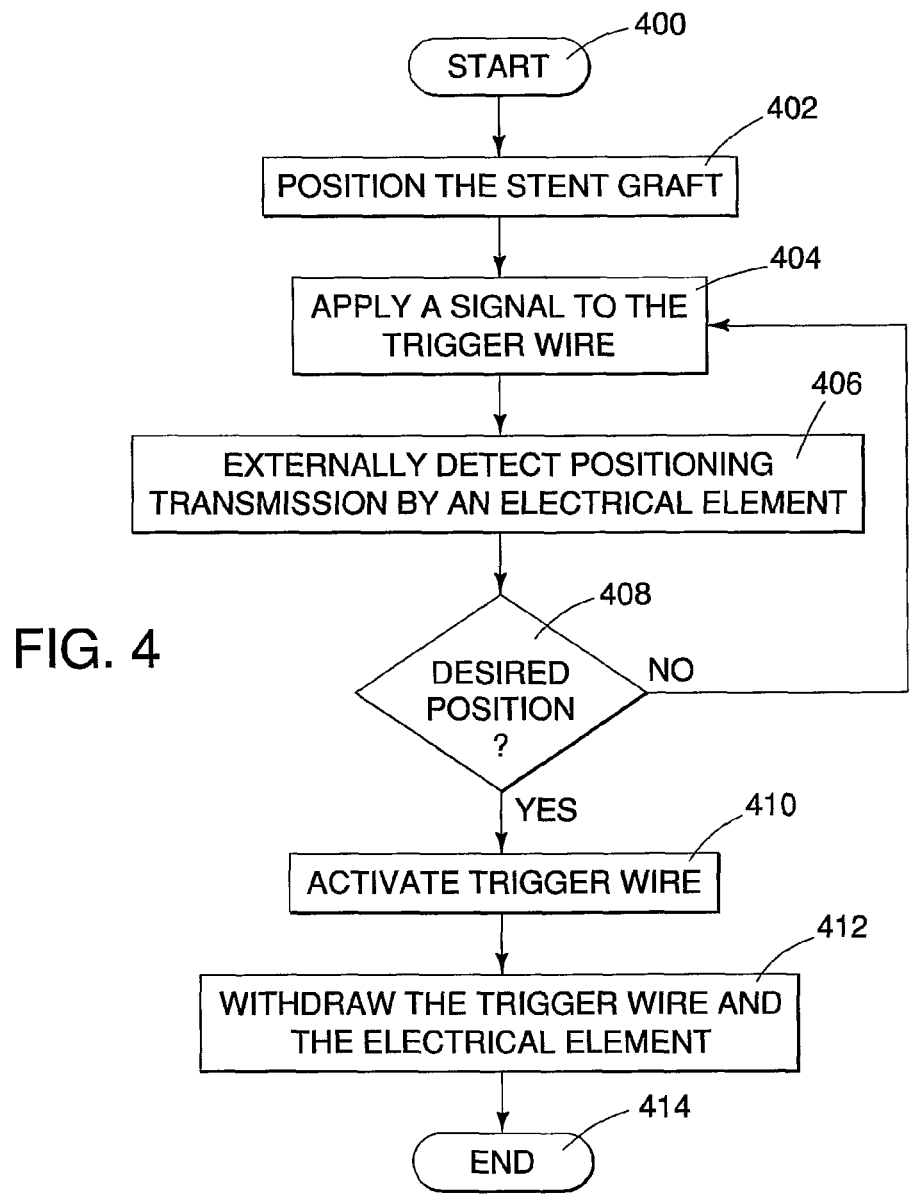
FIG. 4 is a flow diagram illustrating a method for deploying an endovascular prosthetic device.

FIG. 4 is a flow diagram illustrating a method for deploying an endovascular prosthetic device. The method begins at block 400. In one exemplary embodiment, the endovascular prosthetic device is an aortic stent graft to be implanted in the aorta of a human patient at risk of aortic aneurysm. The aortic stent graft includes electrical elements disposed thereon and trigger wires which releasably constrain a mechanical aspect of the stent graft such as its diameter. The trigger wires are dual-purpose in that, in addition to controlling the mechanical constraints, the trigger wires are used to supply power or signals to the electrical elements on the stent graft or to receive signals or data from the electrical elements, such as for positioning the stent graft.

At block 402, the stent graft is positioned near a desired deployment location in a body of a patient. This is typically done transvascularly by introducing the stent graft through a vascular aperture and moving the stent graft toward the desired deployment location. The desired deployment location is based on the pathological condition to be treated and related anatomical considerations. For example, for treatment of vascular disease in the aortic arch, the stent graft must be positioned in a portion of the arch near the aneurysm and with suitable openings aligned to provide for blood flow to the innominate artery, the left common carotid artery and the left subclavian artery. The stent graft may be approximately positioned using conventional techniques by a surgeon.

At block 404, a signal is applied to one or more trigger wires. The nature of the signal applied is based on the nature of the electrical element which is in communication with the selected trigger wire. For example, the electrical element may respond to an applied voltage by emitting a radio frequency transmission of electromagnetic energy. Alternatively, the electrical element may respond to digital data provided on a data bus of one or more conductors. Still further, the electrical element may respond to an impressed current by radiating energy like an antenna for detection and processing outside the body. Accordingly, a voltage or current signal may be applied directly to an electrical portion or electrical conductor of the trigger wire, or the voltage or current may be applied indirectly by inducing an electrical current or voltage on the electrical conductor.

In an alternative embodiment, an optical fiber is part of the trigger wire and the applied signal is optical in nature. The applied signal may include digital data modulating light pulses in the optical fiber or any other optical signal suitable to actuate the electrical element disposed on the stent graft. In some applications, the applied signal may include an electrical signal applied to an electrical portion or electrical conductor of the trigger wire and an optical signal applied to an optical fiber of the trigger wire. In these applications, the trigger wire may be considered to include a bundle of mechanical actuator, electrical conductor and/or optical fiber.

At block 406, a positioning transmission transmitted by the electrical element based on the applied signal is detected. Any suitable detection may be used and should be based on the nature of the transmission induced on the electrical element. For example, the electrical element may be designed to emit a radio signal at a predetermined frequency a predetermined time after being stimulated by the applied signal. Detection of the transmission would involve monitoring the predetermined frequency to receive the radio transmission. The radio transmission may further involve encoding data and modulating a carrier with the encoded data as the electromagnetic positioning transmission. A receiver may detect this positioning transmission by demodulating the received signal and decoding the data. The reception method of the signal generally matches the transmission thereof.

At block 408, it is determined if the stent graft is in the desired position. This may be a manual process by the surgeon implanting the stent graft, using the disclosed apparatus and method along with medical experience. For example, the signal detected at block 406 may be used to produce a display on a display device. By monitoring the display, the surgeon may conclude that the stent graft is correctly positioned. Alternatively, the surgeon may conclude that the stent graft is not positioned correctly and may continue adjusting the position. Still further, the signal may be processed automatically by a data processing system to determine the correctness of the position, and provide this information to the surgeon.

If the result of the decision in block 408 is negative, control returns to block 404. There, a signal is reapplied to the trigger wire and to cause the electrical element to emit another positioning transmission. At the detector, the subsequent electromagnetic positioning transmission transmitted by the electrical element is detected, block 406. Control may remain in the loop including blocks 404, 406, 408 until the stent graft is suitably positioned in the desired deployment location. When the stent graft is suitably positioned, control exits the loop and proceeds to block 410.

At block 410, the trigger wire is activated to release a mechanical constraint of the stent graft or other endovascular prosthetic device and to thereby deploy the stent graft at the desired deployment location. In a typical embodiment, multiple trigger wires are used such as one or more at the proximal end of the stent graft and one or more at the distal end of the stent graft. Activating the trigger wires places the stent graft at its operational position.

At block 412, the trigger wire and the electrical wire associated therewith are withdrawn from the patient. The method ends at block 414.

Figure 5:
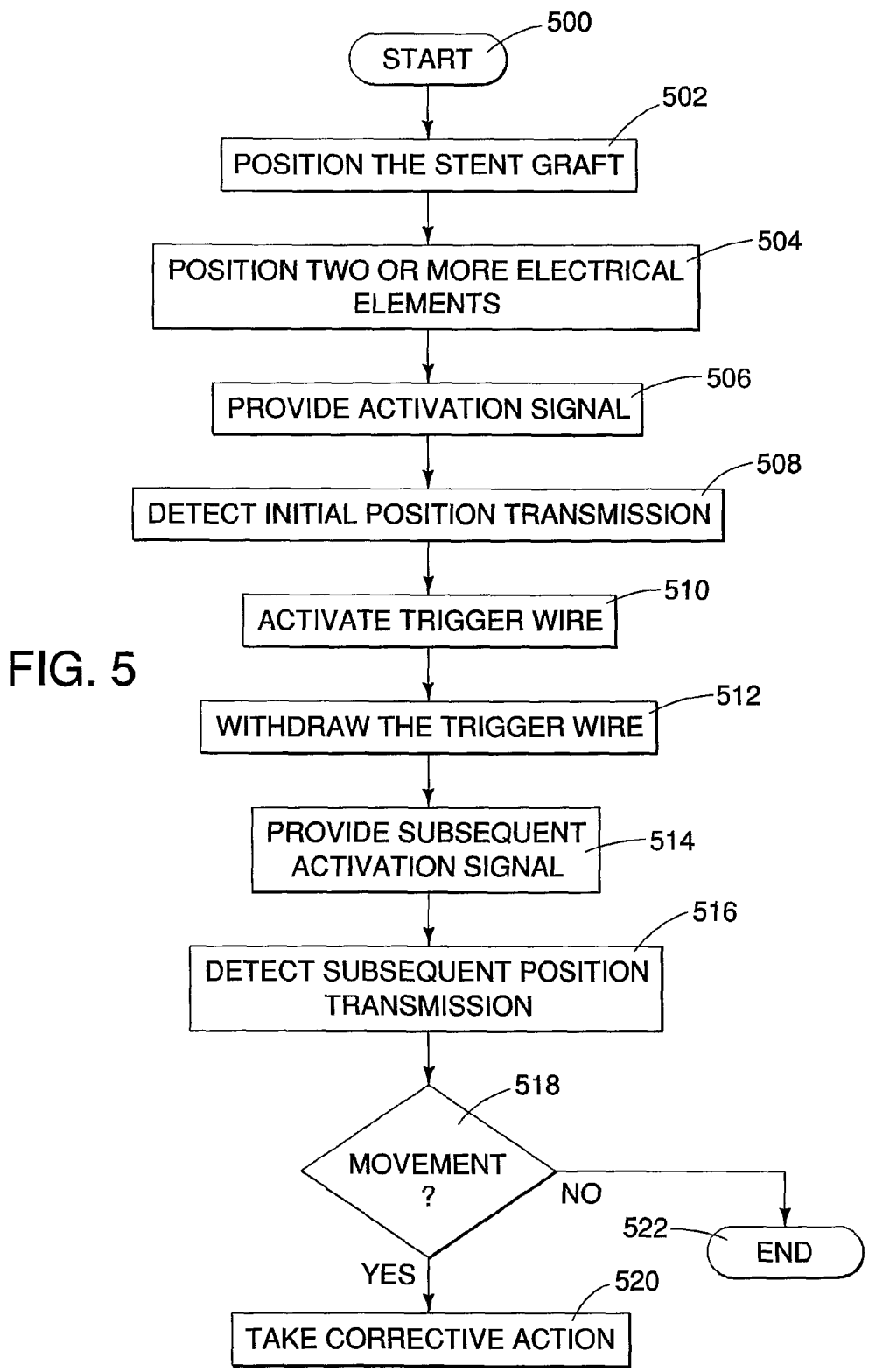
FIG. 5 is a flow diagram illustrating an alternative method for deploying an endovascular prosthetic device.

FIG. 5 is a flow diagram illustrating an alternative method for deploying an endovascular prosthetic device. The embodiment of FIG. 5 is particularly well adapted for longer term monitoring of the placement of an endovascular prosthetic device. For example, some prosthetic devices may migrate over time due to various causes. This can be problematic for long term patient care. For example, if an aortic arch stent graft migrates so that it is no longer aligned with one or more of the innominate artery, the left common carotid artery or the left subclavian artery, the patient's health may be severely impacted. Alternatively, some modular prostheses are used in some applications, where a first prosthesis is joined to a second prosthesis and the two must maintain common connection to avoid endoleaks or other conditions. Long term monitoring may detect migration or separation of the modules.

In these examples, it is important to be able to monitor prosthesis position and detect any migration. In the past, such monitoring has been done by means such as computer assisted tomography (CAT) scans. However, in addition to being costly, time consuming and uncomfortable for some patients, such techniques require a substantial irradiation of the patient which is undesirable. The method of FIG. 5 permits a better alternative.

The method begins at block 500. At block 502, an endovascular prosthetic device is generally positioned in the human body of a patient. For this exemplary embodiment, the example of an aortic arch stent graft is used but the illustrated techniques may be used with a wide variety of devices. The stent graft is positioned by introducing the stent graft vascularly using a suitable endovascular graft delivery system.

At block 504, two or more electrical elements are positioned adjacent to the endovascular prosthetic device or stent graft. Preferably, the electrical elements are disposed on the surface of a stent graft or other prosthesis and are in signal communication with respective trigger wires. The trigger wires are used to mechanically actuate one or more constraints of the prosthesis. Preferable, the electrical elements are detachable from the trigger wires to remain with the prosthesis when the trigger wires are withdrawn. Further, the electrical elements are also electrically responsive to an activation signal conveyed by the respective trigger wires to transmit respective electromagnetic positioning transmissions which are detectible outside the human body. As discussed above in connection with FIGS. 2 and 3, the electrical elements and activation signals may be of any suitable type, including electrical, magnetic or optical. The same is true with the electromagnetic positioning transmissions emitted by the electrical elements. Moreover, so that the electrical elements may be actuated after the trigger wires are withdrawn, the electrical elements may also be responsive to electromagnetic energy impinging on the electrical elements. This may be, for example, radio frequency energy at a predetermined frequency to actuate the electrical elements, similar to radio frequency identification (RFID) devices, or any other suitable method.

At block 506, with the prosthesis generally positioned near a desired deployment location, an activation signal is provided to the trigger wires to activate the electrical elements. As discussed above, this may be an electromagnetic, optical or other type of signal. Providing the signal causes the electrical elements to transmit an initial position transmission.

At block 508, an initial position transmission is detected external to the body of the patient. This may be achieved in any suitable manner, such as detecting a radio frequency transmission from the electrical elements and suitably processing the transmission. If necessary, the stent graft position may be adjusted to precisely locate the stent graft at the desired deployment location, and the process of activating the electrical elements and receiving their transmissions may be repeated. Also, if a modular stent graft is being used, the process may be repeated to ensure that the separate modules are each properly positioned and aligned.

At block 510, with the stent graft in the desired deployment location, the trigger wires are activated to release the constraints on the stent graft. At block 512, the trigger wires are withdrawn from the patient and, as noted above, preferably, the electrical elements remain with the stent graft within the patient. In one embodiment, the remaining electrical element or elements are the same as the electrical elements that are activated by signals applied to the trigger wires. In another embodiment, the remaining elements are different from and separately activated. For example, the electrical elements which are responsive to the activation signal on the trigger wires may be withdrawn, leaving behind a separate set of electrical elements responsive to an externally applied signal, such as radio frequency energy.

The remaining electrical elements may be disposed in any suitable location, but preferably are located so as to permit monitoring of long-term variations such as migration of the prosthetic device or other failure modes. For example, the electrical elements may be positioned in an overlapping orientation so that any migration may be detected. Alternatively, if a modular graft is used, a first electrical element may be used on one module of the stent graft and a second electrical may be used on a second module so that the positional relationship between the two electrical elements may be monitored. Variation in the positions of the electrical elements will be evidence of variation in the position of the modules themselves. In another embodiment, the electrical elements may emit one or more transmissions that are indicative of distance between the electrical elements. By monitoring these transmissions and the distance indicated, the longer-term positioning of the stent graft or modules may be monitored.

At block 514, a subsequent activation signal is applied to the remaining electrical elements. Based on this subsequent activation signal, the remaining electrical elements emit a subsequent position transmission. At block 516, the subsequent position transmission is detected external to the human body. The transmission is processed to identify any movement of the implanted stent graft, block 518. If movement is detected, corrective action may be taken, block 520. Corrective action may be any suitable follow-on practice from further monitoring to surgery and removal and re-implantation of the stent graft. If no movement, or insignificant movement, has been detected, the method ends at block 522.

The description herein can be readily extended to other embodiments. One exemplary embodiment provides the following:

1. A method for an endovascular prosthetic device, the method comprising:

transvascularly positioning an endovascular prosthetic device near a desired deployment location in a human body;

positioning two or more electrical elements adjacent to the endovascular prosthetic device, the two or more electrical elements being in signal communication with two or more respective trigger wires and being electrically responsive to an activation signal conveyed by the respective trigger wires to transmit respective electromagnetic positioning transmissions which are detectible outside the human body;

providing the activation signal to the two or more trigger wires to activate the two or more electrical elements;

detecting initial positioning transmissions to identify an initial position for the endovascular prosthetic device;

subsequently, providing a subsequent activation signal to activate the two or more electrical elements; and detecting subsequent positioning transmissions responsive to the subsequent electromagnetic identifications to identify a movement of the endovascular prosthetic device.

2. The method as in 1 wherein providing the activation signal comprises providing an electrical activation signal on an electrically conducting portion of a respective trigger wire.

3. The method as in 1 wherein providing the activation signal comprises providing an optical activation signal on an optical fiber of a respective trigger wire.

4. The method as in 1 further comprising:

when the endovascular prosthetic device is positioned at a desired deployment position based on the detected positioning transmissions, mechanically activating the two or more respective trigger wires to remove respective mechanical constraints, thereby deploying respective portions of the endovascular prosthetic device.

5. The method as in 4 further comprising:

when the endovascular prosthetic device is fully deployed, withdrawing the two or more respective trigger wires from the human body but allowing the two or more electrical elements to remain in the human body.

From the foregoing, it can be seen that the present invention provides a method and apparatus for utilizing the trigger wires of an endovascular delivery system to supply power and control signals to electrical elements such as sensors attached to a stent graft or delivery system, and to use the trigger wires as transmitting antennas for intra-operative positioning of endovascular devices. An endovascular graft may be attached to a delivery system via trigger wires. These trigger wires attach the graft proximally and distally to the delivery system. Usually, two or more wires attach the stent graft proximally and one wire distally. The trigger wires can serve a dual purpose. Along with securing the device to the delivery system, they can be utilized to power sensors that are attached to the stent graft and/or the device's delivery system, or to act as a transmitting antenna. The transmitting devices may be used for positioning the device in vivo via an intra-operative positioning system. The sensors or trigger wires are attached, for example, to a fenestrated device. The trigger wires allow signals or power to be supplied allowing signals to be transmitted from the device to an external positioning system, allowing the surgeon to visually position the fenestration or series of fenestrations relative to their respective target vessels through a video monitor. The trigger wires exit the distal end of a delivery system and are attached to a power supply, signal generator or similar device. After the graft is positioned and deployed, the trigger wires are removed distally through the delivery system. Benefits include accurate positioning of the stent graft at the desired deployment location and reduced use and incidence of possibly harmful radiation.

While particular embodiments of the present invention have been shown and described, modifications may be made. It is therefore intended that the foregoing detailed description be regarded as illustrative rather than limiting, and that it be understood that it is the following claims, including all equivalents, that are intended to define the spirit and scope of this invention.

The invention claimed is:

1. An endovascular graft delivery system comprising:
   an endovascular prosthetic device;
   one or more trigger wires engaging portions of the endovascular prosthetic device, the one or more trigger wire configured to remove a mechanical constraint from the endovascular medical device upon triggering to thereby deploy the endovascular prosthetic device at a deployment location inside a body of a patient; and
   an electrical element positioned on the endovascular prosthetic device, the electrical element in signal communication with a trigger wire of the one or more trigger wires to communicate operational signals with the trigger wire.

2. The endovascular graft delivery system of claim 1 wherein the operational signals comprise electrical signals or optical signals or both.

3. The endovascular graft delivery system of claim 1 wherein the electrical element is configured to be powered by an electrical signal applied to an electrically conducting portion of the trigger wire.

4. The endovascular graft delivery system of claim 1 wherein the electrical element provides feedback information to the trigger wire when the endovascular prosthetic device is positioned in a body of a patient.

5. The endovascular graft delivery system of claim 4 wherein the trigger wire comprises an electrically conducting trigger wire and wherein the feedback information comprises electrical signals conveyed on the electrically conducting trigger wire, or wherein the trigger wire comprises an optical fiber and wherein the feedback information is optically communicated on the optical fiber.

6. The endovascular graft delivery system of claim 4 wherein the electrical element comprises a sensor to provide information to the trigger wire about a position of the endovascular prosthetic device during deployment of the endovascular prosthetic device in a body of a patient, the information being detectable over the trigger wire at a location outside the body of the patient.

7. The endovascular graft delivery system of claim 1 wherein the electrical element comprises a transmitter responsive to an operational signal received over the trigger wire to emit a positioning transmission.

8. The endovascular graft delivery system of claim 7 wherein the transmitter emits radio frequency energy, magnetic energy or light as the positioning transmission, the positioning transmission being detectable external to the body to locate the endovascular prosthetic device within the body.

9. An endovascular graft delivery system comprising:
   an endovascular graft positionable in a human body;
   one or more electrical elements responsive to an applied operational signal to transmit an electromagnetic transmission, the one or more electrical elements positioned at a proximal end of the endovascular graft delivery system; and
   one or more trigger wires, each respective trigger wire in signal communication with a respective electrical element to provide the operational signal to the respective electrical elements, each respective trigger wire further engaging a portion of the endovascular graft to remove a mechanical constraint from the endovascular graft upon triggering to thereby deploy the endovascular graft, the one or more trigger wires exiting a distal end of the endovascular graft delivery system.

10. The endovascular graft delivery system of claim 9 further comprising:
    a receiver external to the human body operative to receive the transmitted electromagnetic transmission; and
    a display device coupled with the receiver to produce a positioning image based on the received electromagnetic transmission and stored data about the human body.

11. The endovascular graft delivery system of claim 9 wherein the one or more trigger wires comprise an optical fiber.

12. The endovascular graft delivery system of claim 9 wherein the one or more trigger wires comprise and electrical wire bundled with an optical fiber.

13. An endovascular graft delivery system comprising:
    an endovascular prosthetic device;
    one or more trigger wires engaging portions of the endovascular prosthetic device, each trigger wire of the one or more trigger wires configured to remove respective mechanical constraints from the endovascular medical device upon triggering to thereby deploy the endovascular prosthetic device at a deployment location inside a body of a patient; and
    a sensor positioned on the endovascular prosthetic device, the sensor in signal communication with a trigger wire of the one or more trigger wires to provide position information to the trigger wire about a position of the endovascular prosthetic device during deployment of the endovascular prosthetic device in the body of the patient, the information being detectable over the trigger wire at a location outside the body of the patient.

14. The endovascular graft delivery system of claim 13 wherein the sensor is configured to detect one or more conditions and, based on the detected condition, to provide electrical signals to the one or more trigger wires.

15. The endovascular graft delivery system of claim 13 wherein the sensor is configured to detect electromagnetic energy impinging on the sensor from outside the body of the patient and, in response to the detected electromagnetic energy, provide the electrical signals to the trigger wire.

16. The endovascular graft delivery system of claim 13 wherein the trigger wire of the one or more trigger wires is configured to communicate voltage or current or both from the sensor to a detector located outside the body of the patient.

17. The endovascular graft delivery system of claim 13 wherein the trigger wire of the one or more trigger wires is configured to communicate digital data from the sensors to a detector located outside the body of the patient.

* * * * *